United States Patent
Saito et al.

(10) Patent No.: US 7,718,446 B2
(45) Date of Patent: May 18, 2010

(54) EVALUATION METHOD FOR CRYSTAL DEFECT IN SILICON SINGLE CRYSTAL WAFER

(75) Inventors: Hisayuki Saito, Fukushima (JP); Yutaka Kitagawara, Fukushima (JP)

(73) Assignee: Shin-Etsu Handotai Co., Ltd., Tokyo (JP)

(*) Notice: Subject to any disclaimer, the term of this patent is extended or adjusted under 35 U.S.C. 154(b) by 325 days.

(21) Appl. No.: 11/883,184

(22) PCT Filed: Jan. 23, 2006

(86) PCT No.: PCT/JP2006/000948

§ 371 (c)(1),
(2), (4) Date: Jul. 27, 2007

(87) PCT Pub. No.: WO2006/080271

PCT Pub. Date: Aug. 3, 2006

(65) Prior Publication Data

US 2008/0153186 A1    Jun. 26, 2008

(30) Foreign Application Priority Data

Jan. 31, 2005    (JP)    ............................. 2005-023898

(51) Int. Cl.
*H01L 21/00*    (2006.01)
*H01L 21/66*    (2006.01)

(52) U.S. Cl. ........................................... 438/7; 438/16

(58) Field of Classification Search ................. 438/7, 438/16; 257/E21.53
See application file for complete search history.

(56) References Cited

U.S. PATENT DOCUMENTS 7,164,148 B2 *    1/2007    Yoshida et al. ............... 257/13
2005/0231733 A1 *    10/2005    Pfaff et al. ................... 356/517

FOREIGN PATENT DOCUMENTS

| JP | A 10-153555 | 6/1998 |
| JP | A 10-197423 | 7/1998 |
| JP | A 11-079889 | 3/1999 |
| JP | A 2004-259779 | 9/2004 |

OTHER PUBLICATIONS

K. Moriya, "Observation of Defects in Crystals by Laser Tomography", Oyo Butsuri, vol. 55, No. 6, 1986, pp. 542-569.

* cited by examiner

*Primary Examiner*—William M. Brewster
(74) *Attorney, Agent, or Firm*—Oliff & Berridge, PLC

(57) ABSTRACT

The present invention provides an evaluation method for a crystal defect in a silicon single crystal wafer based on an infrared laser scattering tomograph method, wherein at least, the silicon single crystal wafer is irradiated with a laser beam, and light that enters the silicon single crystal wafer is scattered by a crystal defect, and the scattered light is detected to evaluate a Direct Surface Oxide Defect (DSOD) and a void defect smaller than the DSOD in the silicon single crystal wafer. As a result, the evaluation method for a crystal defect in a silicon single crystal wafer that can simply and precisely evaluate, e.g., a small DSOD, which can be conventionally evaluated based on a Cu deposition method alone, without requiring a wasteful cost.

12 Claims, 4 Drawing Sheets

(a)

(b)

EVALUATION METHOD FOR CRYSTAL DEFECT IN SILICON SINGLE CRYSTAL WAFER

TECHNICAL FIELD

The present invention relates to an evaluation method for a crystal defect in a silicon single crystal wafer that serves as a substrate for manufacturing, e.g., a semiconductor integrated circuit.

BACKGROUND ART

Silicon single crystal wafers are used mostly as materials forming a semiconductor integrated circuit. Various kinds of stresses are applied to a wafer by a heat treatment or machining until a semiconductor device is formed on a surface layer of a silicon single crystal wafer to provide an integrated circuit. Therefore, a silicon single crystal wafer produced from a silicon single crystal obtained by a Czochralski method (which will be referred to as a CZ method hereinafter) is superior in strength, and hence this wafer tends to be often used.

However, in recent years, with density growth of an integration degree of a semiconductor integrated circuit and attendant miniaturization of a device circuit, a quality requirement for a silicon single crystal as a wafer material is rigidifying. In particular, a grown-in defect that is introduced into a crystal at the time of growing a silicon single crystal has a great effect on characteristics when an integrated circuit is formed on a surface layer of the silicon single crystal wafer, and hence the defect present in the surface layer of a wafer used as a material for a high-function semiconductor device is precisely specified to product the silicon single crystal wafer. Further, in order to fulfill this requirement, in production of a silicon single crystal as a material of the silicon single crystal wafer, various methods of growing a silicon single crystal that can suppress formation of the grown-in defects as much as possible (that can ideally prevent the grown-in defects from being formed at all or can suppress such defects with a very low density even though the defects are formed) have been examined.

In order to grow a low-defect crystal in which the grown-in defect is suppressed, growing the crystal while preferably keeping a cooling rate of the single crystal pulled from a raw material melt constant as much as possible in an area where a defect formation suppressing effect becomes prominent. As disclosed in, e.g., Japanese Patent Laid-open (Kokai) No. H11-79889, when a crystal is grown in a neutral region which is present at a boundary between a V-rich region where a grown-in defect, e.g., a Flow Pattern Defect (FPD), a Laser Scattering Tomography Defect (LSTD), or a Crystal Originated Particle (COP) is generated and an I-rich region where a Large-Secco Etch Pit Defect (L-SEPD) is generated and in which these crystal defects are not present, a silicon single crystal having a high quality can be obtained.

In recent years, a demand for a high-quality silicon single crystal wafer in which crystal defects are suppressed as explained above has been increased. However, it has been revealed that very small crystal defects are present even in a silicon single crystal subjected to crystal growth in a neutral region to suppress such crystal defects. Since such a crystal defect has a very small defect size (a diameter: approximately 15 nm to 20 nm), a particle counter used for regular crystal examination cannot detect such crystal defects. These defects are called Direct Surface Oxide Defects (DSOD), and detected by defect evaluation using Cu (copper) deposition.

The Cu deposition method has characteristics of accurately measuring defect positions in a silicon single crystal and improving a detection limit with respect to defects present in a wafer surface layer, thereby precisely evaluating very small defects. Specifically, an oxide insulating film (which will be also simply referred to as an oxide film hereinafter) having a predetermined thickness is formed on a wafer surface, and the oxide insulating film provided above a position of a defect formed in the wafer surface layer is destructed. Further, Cu is deposited at a position of the destructed oxide film part to specify the defect. When a voltage is applied to the oxide film formed on the wafer surface in a solution in which a Cu ion is present, a current flows through a part where the oxide film is degraded, and the Cu ion is precipitated as Cu. Since it is known that a the Cu precipitation part is a part where a grown-in defect due to a void, e.g., a COP is present, when this part is observed under a collimated light or directly by the naked eye or observed through an optical microscope, a transmission electron microscope (TEM), or a scanning electron microscope (SEM), a distribution or a density of defects can be evaluated.

Although the DSOD can be confirmed by evaluation based on the Cu deposition method, a surface of the wafer must be machined into a mirror surface in evaluation based on the Cu deposition method, and this is usually carried out in the form of sampling inspection after a mirror polishing process that is a final process in wafer processing. However, when the wafer is rejected on this stage, wafer machining is performed even with respect to a rejected lot without exception, and the rejected product takes labor and cost like a conforming product but is finally discarded, which is hence wasteful. Furthermore, the defect is hard to be discriminated from, e.g., a scratch caused by machining, and hence there is a problem in a measurement precision.

As explained above, the DSOD is a small defect having a diameter of approximately 15 to 20 nm, but a void defect (a diameter: approximately 10 to 15 nm) smaller than the DSOD may present in a surface layer of a silicon single crystal wafer. This small void defect may also affect characteristics of an integrated circuit formed on the surface layer of the silicon single crystal wafer in some cases. Therefore, a method that enables accurate and simple evaluation with respect to this void defect smaller than the DSOD has been demanded.

DISCLOSURE OF INVENTION

In view of the above-explained problem, it is an object of the present invention to provide an evaluation method for evaluating a crystal defect in a silicon single crystal wafer, which can simply and precisely evaluate, e.g., a small DSOD that can be conventionally evaluated by the Cu deposition method alone without requiring a wasteful cost.

To achieve this object, the present invention provides an evaluation method for a crystal defect in a silicon single crystal wafer based on an infrared laser scattering tomograph method, wherein at least, the silicon single crystal wafer is irradiated with a laser beam, and light that enters the silicon single crystal wafer is scattered by the crystal defect, and the scattered light is detected to evaluate a DSOD (Direct Surface Oxide Defect) and a void defect smaller than the DSOD in the silicon single crystal wafer.

According to the present invention, a small DSOD that is conventionally considered to be evaluated by the Cu deposition method alone is evaluated based on the infrared laser scattering tomograph method that is simpler than the Cu deposition method. Therefore, according to the present invention, a DSOD and a void defect (a diameter: approximately 10 nm) smaller than the DSOD can be evaluated at a lower cost. Further, according to the infrared laser scattering tomograph method, a small DSOD and a void defect (a diameter: approximately 10 nm) smaller than the DSOD can be precisely evaluated.

Furthermore, in the evaluation method for a crystal defect in a silicon single crystal wafer according to the present invention, it is preferable that an intensity of the laser beam to be irradiated is set to 300 mW or above.

When the intensity of the laser beam to be irradiated is set to 300 mW or above, a small DSOD and a void defect smaller than the DSOD can be further assuredly detected.

Moreover, in the evaluation method for a crystal defect in a silicon single crystal wafer according to the present invention, it is preferable that the scattered light is detected by a CCD (Charge-Coupled Device).

As described above, the scattered light scattered by a crystal defect is detected by using the Charge-Coupled Device (CCD), a detection sensitivity for the scattered light can be further increased, and a small DSOD and a void defect smaller than the DSOD can be further accurately evaluated.

Additionally, in the evaluation method for a crystal defect in a silicon single crystal wafer according to the present invention, a silicon single crystal wafer to be evaluated is made without performing mirror polishing by at least slicing the silicon single crystal wafer from a silicon single crystal, subjecting the sliced silicon single crystal wafer to surface grinding or lapping, and etching the surface-ground or lapped silicon single crystal wafer.

That is, in the present invention, since a DSOD is evaluated based on the infrared laser scattering tomograph method, a surface of the wafer does not have to be processed into a mirror surface, and evaluation can be effected before the mirror polishing step as a final step, i.e., in an intermediate step. Therefore, an unfruitful work, i.e., taking a labor and a cost till the last mirror polishing step to be ended up in disposal is not produced. Additionally, a DSOD and a void defect smaller than the DSOD can be discriminated from, e.g., a scratch caused by processing, thereby improving a measurement accuracy.

Further, in the evaluation method according to the present invention, it is preferable that a central part of the silicon single crystal wafer to be evaluated is cleaved, a main surface of the silicon single crystal wafer is irradiated with the laser beam, and the scattered light is detected from the cleaved surface of the silicon single crystal wafer.

In this manner, when the main surface of the silicon single crystal wafer is irradiated with the laser beam to detect the scattered light from the cleaved surface of the silicon single crystal wafer, presence/absence of a DSOD and a void defect smaller than the DSOD can be accurately evaluated.

Furthermore, in this case, it is preferable that scanning is performed while irradiating the main surface of the silicon single crystal wafer with the laser beam at fixed intervals.

When scanning is carried out while irradiating the main surface of the silicon single crystal wafer with the laser beam at fixed intervals, an entire region of the wafer in a radial direction can be evaluated in a shorter time.

As explained above, according to the present invention, since small void defects including DSODs in the silicon single crystal wafer are evaluated based on the infrared laser scattering tomograph without using the Cu deposition method, the small void defects can be simply and further precisely evaluated without requiring a wasteful cost.

BEST MODES FOR CARRYING OUT THE INVENTION

Figure 1:
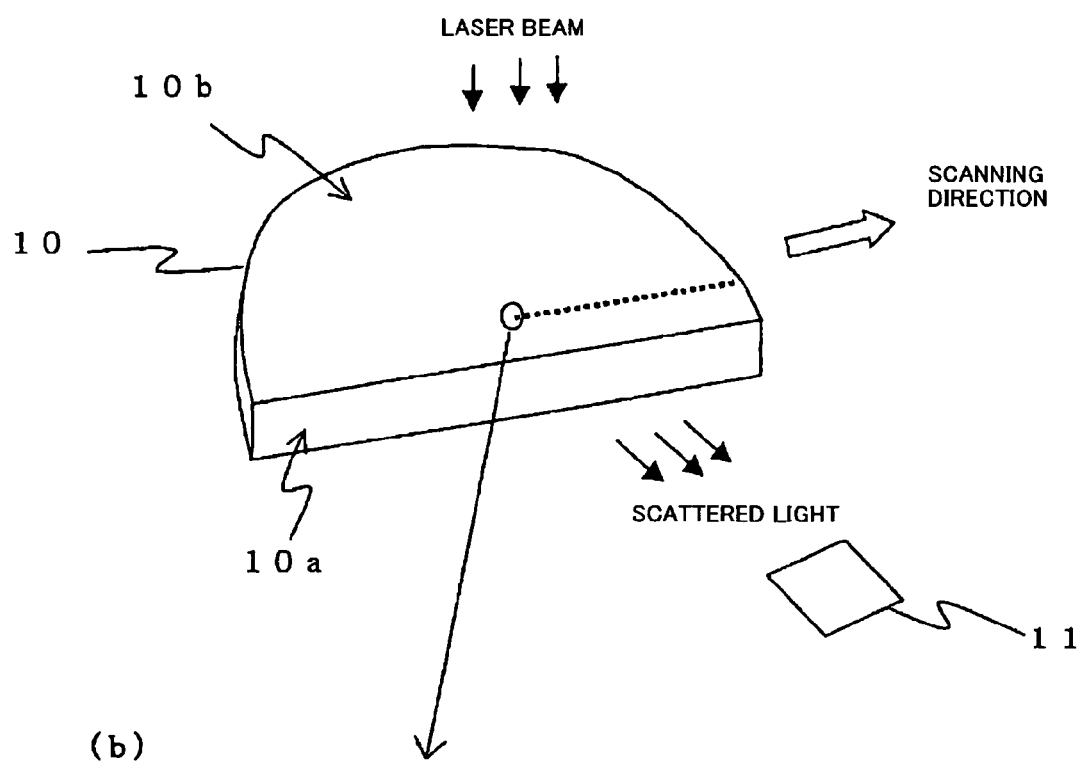
FIG. 1 is an explanatory view for explaining an example of an evaluation method for a crystal defect in a silicon single crystal wafer according to the present invention.
Figure 1:
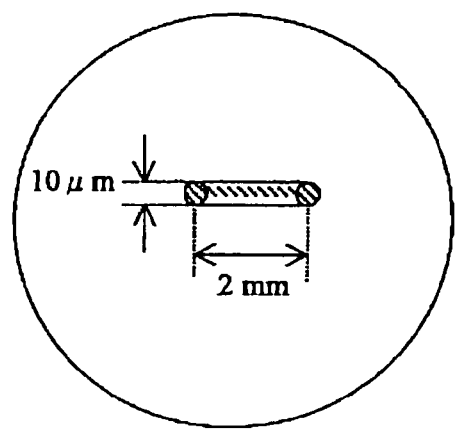

The present intention will now be explained.

As explained above, since a DSOD is a very small defect having a diameter size of 20 nm or below, especially a diameter of approximately 15 to 20 nm, a particle counter and others used for evaluation of a regular crystal defect cannot detect the DSOD, and the DSOD has been conventionally evaluated by a Cu deposition method. However, the Cu deposition method has problems to be solved, i.e., simplicity, a cost, a detection precision, and others. Thus, the present inventor has positively repeatedly performed examination to develop a method that enables simply evaluating the DSOD at a low cost with a high precision.

Here, an infrared laser scattering tomograph method has been used to evaluate crystal defects in some cases. This is generally an evaluation method used to evaluate oxygen precipitation after a heat treatment.

The present inventor has paid attention to this infrared laser scattering tomograph method, and positively repeatedly conducted experiments to confirm whether the DSOD as a small defect can be evaluated by the infrared laser scattering tomograph method. That is, although the fact that the DSOD can be detected by this infrared laser scattering tomograph method has not been conventionally known, the present inventor has discovered that increasing an intensity of a laser beam enables heightening an intensity of a scattered light and raising a detection sensitivity for a crystal defect and both a very small defect due to a crystal like a DSOD defect observed by the Cu deposition method and a void defect smaller than the DSOD can be evaluated by the infrared laser scattering tomograph method, thus they accomplished the present invention.

That is, the present invention provides an evaluation method for a crystal defect in a silicon single crystal wafer based on an infrared laser scattering tomograph method, wherein at least, a silicon single crystal wafer is irradiated with a laser beam, and light that enters the silicon single crystal wafer is scattered by the crystal defect, and the scattered light is detected to evaluate a void defect including a DSOD in the silicon single crystal wafer.

Embodiments of the present invention such an evaluation method for a crystal defect in a silicon single crystal wafer will be described with reference to FIG. 1. However, the present invention is not limited thereto.

FIG. 1(a) is a perspective view, and FIG. 1(b) is an enlarged view of a part surrounded by a circle in (a).

A central part of a silicon single crystal wafer 10 used in this example is cleaved. This silicon single crystal wafer 10 is mounted on a stage of an infrared laser scattering tomograph apparatus, and a main surface 10b of the wafer is irradiated with a laser beam. If crystal defects are present in the wafer 10, light is scattered, and hence detecting the scattered light by a detector 11 installed in a direction of the cleaved surface 10a enables evaluating the number or sizes of the crystal defects. At this time, an intensity of the infrared laser beam is usually set to a value higher than a value (not greater than 100 mW) adopted in evaluation of a defect, e.g., a Bulk Micro Defect (BMD), e.g., 300 mW or above. It is to be noted that an upper limit of the intensity of the infrared laser beam is not restricted to a specific value, but setting the upper limit to 4 W or below, especially 1 W or below is practically desirable.

When such an infrared laser scattering tomograph method is used, a DSOD and a void defect smaller than the DSOD can be simply evaluated at a low cost and with a high precision. In particular, when the intensity of the laser beam is set to 300 mW or above, a DSOD and a void defect smaller than the DSOD can be further assuredly detected.

Figure 6:
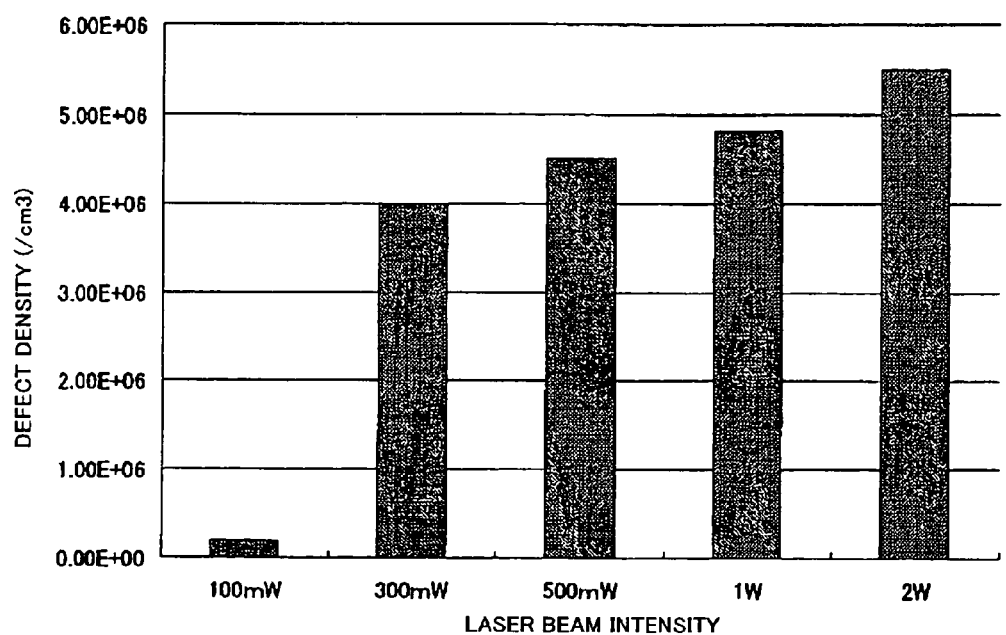
FIG. 6 is a graph showing an experimental result of evaluating defects while changing an intensity of a laser beam.

Here, FIG. 6 is a graph showing an experimental result of evaluating defects while changing an intensity of the laser beam. It can be understood that a DSOD and a small void defect smaller than the DSOD are hardly detected when an intensity of the laser beam is 100 mW or below, but setting the intensity of the laser beam to 300 mW or above enables assured detection.

Furthermore, as the detector 11, there is, e.g., a Charge-Coupled Device (CCD). When this CCD is used to detect the scattered light, the scattered light can be detected with a higher sensitivity, thus further accurately evaluating a DSOD and others.

Here, as the silicon single crystal wafer to be evaluated, one made as follows can be used, for example. That is, a silicon single crystal wafer is made without performing mirror polishing by slicing the silicon single crystal wafer from a silicon single crystal grown by a CZ method, subjecting the sliced silicon single crystal wafer to surface grinding or lapping, and etching the surface-ground or lapped silicon single crystal wafer. Moreover, an oxidation heat treatment does not have to be applied to the wafer like an example where a DSOD is measured by a Cu deposition method.

According to the present invention, since the infrared laser scattering tomograph method is used, a DSOD can be evaluated even if a silicon single crystal wafer that is not subjected to mirror polishing is used. Therefore, the silicon single crystal wafer can be sampled to be evaluated in an intermediate step before the mirror polishing step as a final step, and an unfruitful process, i.e., taking a labor and a cost till the last mirror polishing step and discarding the wafer when it is rejected like a conventional technology is not produced. Additionally, a DSOD and a void defect smaller than the DSOD can be discriminated from a scratch caused by machining, thereby improving a measurement accuracy.

Further, as shown in FIG. 1, the silicon single crystal wafer 10 whose central part is cleaved is used, and the main surface 10b of the silicon single crystal wafer 10 is irradiated with a laser beam to detect scattered light from the cleaved surface 10a of the silicon single crystal wafer 10, thereby accurately evaluating presence/absence of a DSOD and a void defect smaller than the DSOD.

In FIG. 1, the main surface 10b of the silicon single crystal wafer 10 is 2 mm irradiated with a laser beam having an irradiation portion diameter of 10 μm from a wafer center toward an outer periphery, and it is again 2 mm irradiated with the laser beam at a fixed interval. When scanning in the radial direction is carried out while irradiating the main surface of the silicon single crystal wafer with the laser beam at fixed intervals in this manner, an entire region of the wafer in the radial direction can be evaluated in a shorter time.

Hereinafter, the present invention will be explained further in detail with reference to Experiments 1 and 2, however the present invention is not limited thereto.

EXPERIMENT 1

An example of examining a relationship between crystal defects detected by the infrared laser scattering tomograph method according to the present invention and crystal defects detected by the conventional Cu deposition method will be described.

First, a silicon single crystal having a diameter 300 mm and a crystal orientation <100> was pulled upwardly by the CZ method. As crystal growth conditions, and a growth rate was selected in such a manner that DSODs alone are present without an FPD, thereby producing a single crystal.

After silicon single crystal growth, the grown silicon single crystal was ground by a cylindrical grinder to remove a cone part and a tail part of the single crystal, and then a crystal fixed-diameter part was cut into a length of approximately 25 cm to provide a single crystal block.

A wafer of approximately 1 mm was sliced from the cone side of this single crystal block by a slicer, a surface of this wafer was ground approximately 300 μm based on surface grinding, and then the wafer was etched with a mixture containing a hydrofluoric acid, a nitric acid, and an acetic acid. Then, a scratch was made by, e.g., a diamond pen in such a manner that it runs through a central part of the etched wafer, and then the wafer was cleaved and split in two.

Further, the thus made silicon single crystal wafer was attached to an infrared laser scattering tomograph apparatus (a product name: MO-441, manufactured by Mitsui Mining & Smelting Co., Ltd.).

Then, the cleaved surface was irradiated with an infrared laser beam in parallel (vertical to the main surface). The infrared laser beam was irradiated 2 mm from a center of the silicon single crystal wafer toward an outer periphery, then it was again irradiated 2 mm with an interval of 8 mm, and 15 positions were irradiated in this manner. At this time, the irradiated infrared laser beam had a wavelength of 1064 nm and an intensity of 1000 mW, and a diameter of an irradiation area was approximately 10 μm. Moreover, a CCD was installed a position vertical to the cleaved surface of the wafer to detect scattered light, and the infrared laser beam was irradiated to enable detecting the scattered light scattered by a crystal defect.

Figure 2:
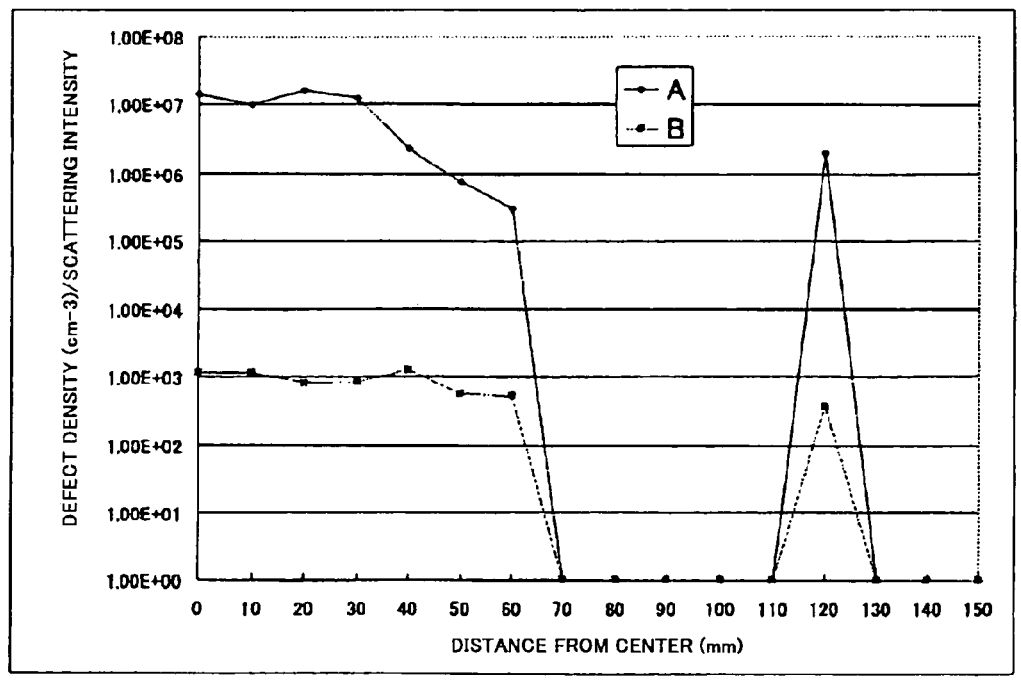
FIG. 2 is a graph showing an example of crystal defect examination based on an infrared laser scattering tomograph method and a Cu deposition method (Experiment 1)

FIG. 2 shows an intensity distribution of the thus detected scattered light (a line graph B in FIG. 2).

Here, horizontal axis in FIG. 2 represents a distance from the wafer center, and vertical axis represents a defect density and a scattering intensity. Moreover, for example, "1.00E+0.8" in the ordinate indicates "$1.00 \times 10^8$".

On the other hand, the remainder of the single crystal block was processed into a plurality of mirror surface wafers via regular product process steps, i.e., a slicing step, a chamfering step, a surface grinding step or a lapping step, an etching step, and a polishing step. One wafer was selected from the plurality of mirror surface wafer based on sampling, an oxide film was formed on a surface of the selected wafer, and then processing based on the Cu deposition method was carried out to measure the number of defects in the wafer surface with the naked eye under a collimated light.

That is, the wafer having the oxide film formed thereon was immersed in a solution where a Cu ion is present, and a voltage was applied to the oxide film formed on the wafer surface. As a result, the oxide film at each position where a DSOD is present was degraded, a current flowed, and the Cu ion was precipitated as Cu. Additionally, this Cu precipitated part was directly observed with the naked eye under the collimated light.

FIG. 2 shows a defect density distribution in the thus obtained wafer surface (a line graph A in FIG. 2). Further, FIG. 3 shows a photograph of the DSODs on the wafer surface elicited by the Cu deposition method.

Figure 3:
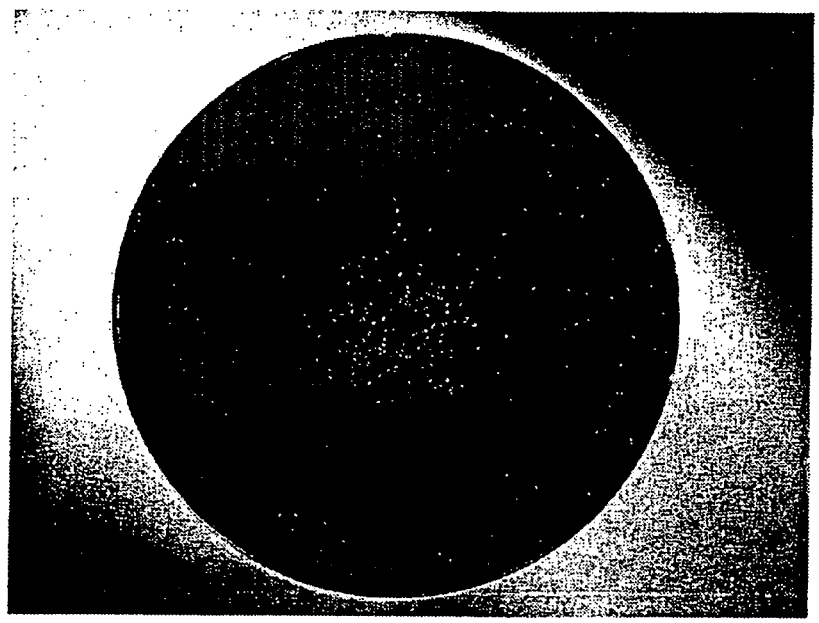
FIG. 3 is a photograph showing an example of DSODs on a wafer surface elicited by the Cu deposition method (Experiment 1)

It can be understood from FIGS. 2 and 3 that the DSODs are present at a central part and an outer peripheral part of this wafer according to the Cu deposition method (the line graph A in FIG. 2). Furthermore, the scattering intensity distribution (the line graph B in FIG. 2) according to the infrared laser scattering tomograph method also demonstrates the similar distribution as this line graph A, and hence it can be understood that the scattering intensity distribution based on the infrared laser scattering tomograph method and the defect density distribution based on the Cu deposition method have a very good correlation.

EXPERIMENT 2

Another example of examining a relationship between crystal defects detected by the infrared laser scattering tomograph method according to the present invention and crystal defects detected by the conventional Cu deposition method will now be explained.

Like Experiment 1, two single crystal blocks (A, B) were cut from a silicon single crystal having a diameter 300 mm and a crystal orientation <100> pulled by the CZ method, and silicon single crystal wafers were sliced from the single crystal blocks (A, B).

Moreover, like Experiment 1, a silicon single crystal wafer for evaluation was made, and evaluation of crystal defects based on the infrared laser scattering tomograph method and evaluation of crystal defects based on the Cu deposition method were carried out.

Figure 4:
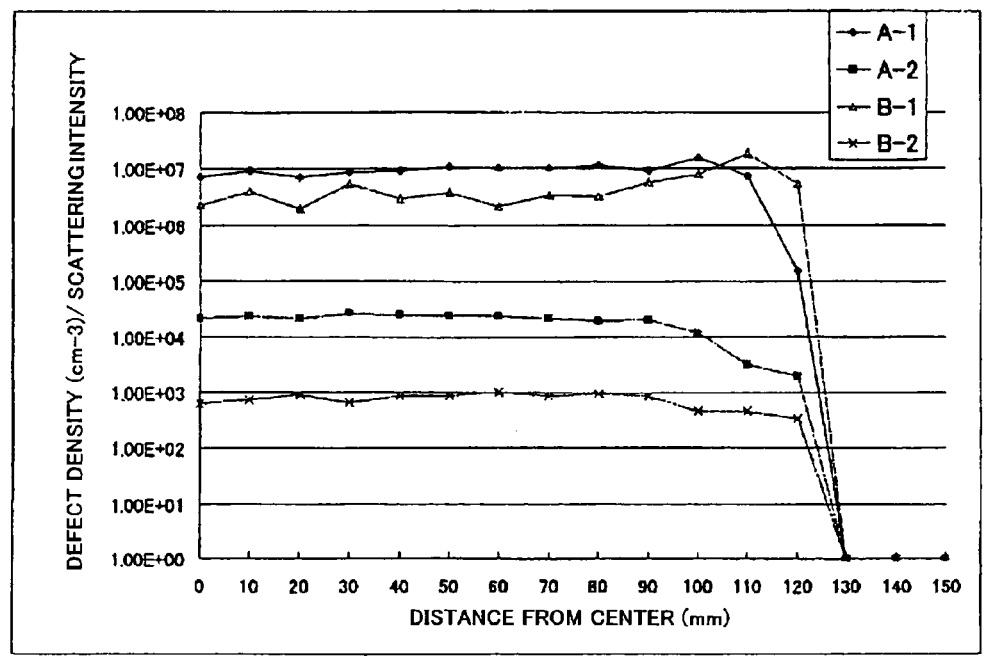
FIG. 4 is a graph showing another example of crystal defect examination based on the infrared laser scattering tomograph method and the Cu deposition method (Experiment 2)

FIG. 4 shows its result. Here, horizontal axis in FIG. 4 represents a distance from the wafer center, and vertical axis represents a defect density and a scattering intensity.

Figure 5:
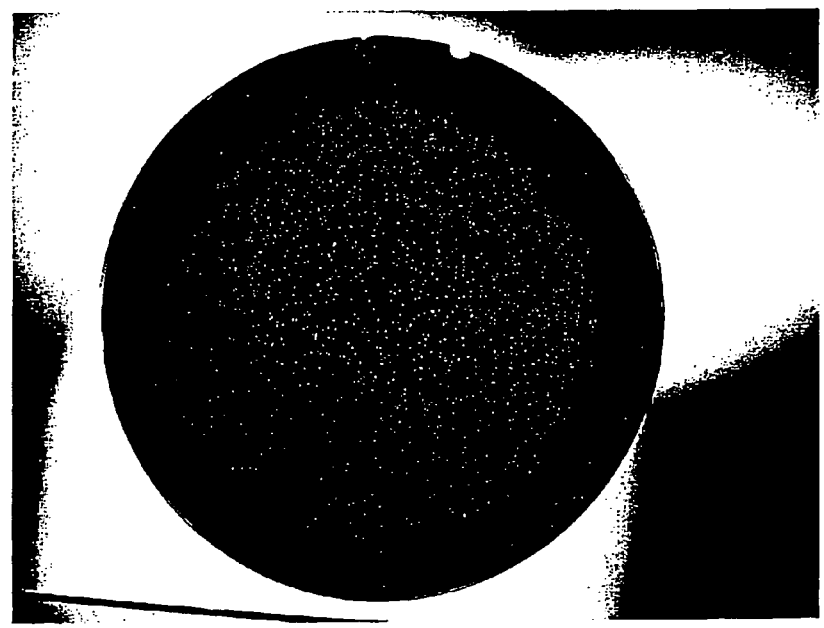
FIG. 5 is a photograph showing another example of DSODs on the wafer surface elicited by the Cu deposition method (Experiment 2)

In FIG. 4, a line graph A-1 indicates a defect density distribution in a wafer surface when the wafer of the block A was evaluated based on the Cu deposition method. It is to be noted that FIG. 5 shows a photograph of DSODs on a wafer surface elicited by the Cu deposition method. Furthermore, a line graph A-2 indicates an intensity distribution of the scattered light in the wafer surface when the wafer of the block A was evaluated based on the infrared laser scattering tomograph method.

On the other hand, in FIG. 4, a line graph B-1 indicates a defect density distribution in the wafer surface when the wafer of the block B was evaluated based on the Cu deposition method. Moreover, a line graph B-2 indicates an intensity distribution of the scattered light in the wafer surface when the wafer of the block B was evaluated based on the infrared laser scattering tomograph method.

It can be understood that the block A (the line graph A-1 in FIG. 4) has a higher DSOD density than the block B (the line graph B-1 in FIG. 4). On the other hand, a scattering intensity of the block A (the line graph A-2 in FIG. 4) based on the infrared laser scattering tomograph method also indicates a value higher than that of the block B (the line graph B-2 in FIG. 4), and it is revealed that quantitative analysis of the DSOD can be also performed based on the infrared laser scattering tomograph method.

It can be understood from these experiments that DSODs can be accurately evaluated by using the infrared laser scattering tomograph method like the present invention without using the Cu deposition method.

Further, as a result of observation using an electron microscope, it was found that void defects (a diameter: 10 to 15 nm) smaller than DSODs can be also evaluated based on the infrared laser scattering tomograph method using a laser beam having an intensity of 300 mW or above.

In addition, the present invention is not limited to the embodiment described above. The above-described aspects are mere examples and those having substantially the same structure as technical ideas described in the appended claims and providing the similar functions and advantages are included in the scope of the present invention.

The invention claimed is:

1. An evaluation method for a crystal defect in a silicon single crystal wafer based on an infrared laser scattering tomograph method, the method comprising:
   irradiating the silicon single crystal wafer with a laser beam whose intensity is set to 300 mW or above, wherein light that enters the silicon single crystal wafer is scattered by the crystal defect;
   detecting the scattered light; and
   evaluating a Direct Surface Oxide Defect and avoid defect smaller than the Direct Surface Oxide Defect in the silicon single crystal wafer.

2. The evaluation method for a crystal defect in a silicon single crystal wafer according to claim 1, wherein the scattered light is detected by a Charge-Coupled Device.

3. The evaluation method for a crystal defect in a silicon single crystal wafer according to claim 1, wherein the silicon single crystal wafer to be evaluated is made without performing mirror polishing by at least slicing the silicon single crystal wafer from a silicon single crystal, subjecting the sliced silicon single crystal wafer to surface grinding or lapping, and etching the surface-ground or lapped silicon single crystal wafer.

4. The evaluation method for a crystal defect in a silicon single crystal wafer according to claim 2, wherein the silicon single crystal wafer to be evaluated is made without performing mirror polishing by at least slicing the silicon single crystal wafer from a silicon single crystal, subjecting the sliced silicon single crystal wafer to surface grinding or lapping, and etching the surface-ground or lapped silicon single crystal wafer.

5. The evaluation method for a crystal defect in a silicon single crystal wafer according to claim 1, wherein a central part of the silicon single crystal wafer to be evaluated is cleaved, a main surface of the silicon single crystal wafer is irradiated with the laser beam, and the scattered light is detected from the cleaved surface of the silicon single crystal wafer.

6. The evaluation method for a crystal defect in a silicon single crystal wafer according to claim 2, wherein a central part of the silicon single crystal wafer to be evaluated is cleaved, a main surface of the silicon single crystal wafer is irradiated with the laser beam, and the scattered light is detected from the cleaved surface of the silicon single crystal wafer.

7. The evaluation method for a crystal defect in a silicon single crystal wafer according to claim 3, wherein a central part of the silicon single crystal wafer to be evaluated is cleaved, a main surface of the silicon single crystal wafer is irradiated with the laser beam, and the scattered light is detected from the cleaved surface of the silicon single crystal wafer.

8. The evaluation method for a crystal defect in a silicon single crystal wafer according to claim 4, wherein a central part of the silicon single crystal wafer to be evaluated is cleaved, a main surface of the silicon single crystal wafer is irradiated with the laser beam, and the scattered light is detected from the cleaved surface of the silicon single crystal wafer.

9. The evaluation method for a crystal defect in a silicon single crystal wafer according to claim 5, wherein scanning is performed while irradiating the main surface of the silicon single crystal wafer with the laser beam at fixed intervals.

10. The evaluation method for a crystal defect in a silicon single crystal wafer according to claim 6, wherein scanning is performed while irradiating the main surface of the silicon single crystal wafer with the laser beam at fixed intervals.

11. The evaluation method for a crystal defect in a silicon single crystal wafer according to claim 7, wherein scanning is performed while irradiating the main surface of the silicon single crystal wafer with the laser beam at fixed intervals.

12. The evaluation method for a crystal defect in a silicon single crystal wafer according to claim 8, wherein scanning is performed while irradiating the main surface of the silicon single crystal wafer with the laser beam at fixed intervals.

* * * * *